US009297769B1

(12) United States Patent
Hill et al.

(10) Patent No.: US 9,297,769 B1
(45) Date of Patent: *Mar. 29, 2016

(54) METHOD FOR REDUCING ALIASING IN TDI BASED IMAGING (71) Applicant: KLA-Tencor Corporation, Milpitas, CA (US)

(72) Inventors: Andrew V. Hill, Sunnyvale, CA (US); David W. Shortt, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/611,874

(22) Filed: Feb. 2, 2015

Related U.S. Application Data (63) Continuation of application No. 13/569,607, filed on Aug. 8, 2012, now Pat. No. 8,947,521.

(60) Provisional application No. 61/521,253, filed on Aug. 8, 2011.

(51) Int. Cl.
G01N 21/88 (2006.01)
H04N 5/217 (2011.01)
H04N 5/232 (2006.01)

(52) U.S. Cl.
CPC ........ *G01N 21/8851* (2013.01); *G01N 21/8803* (2013.01); *H04N 5/217* (2013.01); *H04N 5/23296* (2013.01); *G01N 2021/8887* (2013.01)

(58) Field of Classification Search
CPC .......... G01N 21/8851; G01N 21/8803; G01N 21/9501; G01N 21/956; G01N 2021/8887; H04N 5/217; H04N 5/23296; H04N 5/357; H04N 5/23287
See application file for complete search history.

(56) References Cited

U.S. PATENT DOCUMENTS

| 5,600,138 | A | 2/1997 | Colson et al. |
| 7,465,913 | B2 | 12/2008 | Chuang et al. |
| 7,675,651 | B2 | 3/2010 | Wang et al. |
| 2005/0196059 | A1* | 9/2005 | Inoue et al. ................... 382/240 |
| 2007/0097220 | A1 | 5/2007 | Stavely et al. |
| 2007/0097232 | A1 | 5/2007 | Goris et al. |
| 2010/0188655 | A1 | 7/2010 | Brown et al. |
| 2011/0115903 | A1 | 5/2011 | Shalem et al. |
| 2011/0221886 | A1 | 9/2011 | Nishiyama et al. |
| 2012/0207382 | A1 | 8/2012 | Maeda et al. |
| 2013/0194445 | A1 | 8/2013 | Brown et al. |
| 2014/0043463 | A1 | 2/2014 | Brown et al. |
| 2014/0104468 | A1 | 4/2014 | Parker et al. |

* cited by examiner

Primary Examiner — Brian Yenke
(74) Attorney, Agent, or Firm — Suiter Swantz pc llo

(57) ABSTRACT

The invention may be embodied in a time delay integration (TDI) based sensor wafer inspection system that introduces controlled blur into the sampled image to suppress high spectral frequencies and thereby mitigate the occurrence of aliasing in the sampled image. Image blur may be introduced in the scan direction by desynchronizing the image motion (scan rate) from the charge transfer rate within the TDI sensor (sample clock rate). The scan rate may be desynchronized from the TDI sample clock rate by altering the speed of wafer movement, the sample clock rate, or the magnification of the imaging optics. Image blur may be introduced in the cross-scan direction by imparting a small alignment difference between the direction of image motion (image scan direction) and the direction that charges transfer within the TDI sensor (sensor direction).

22 Claims, 8 Drawing Sheets

METHOD FOR REDUCING ALIASING IN TDI BASED IMAGING

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation patent application of United States Patent Application entitled METHOD FOR REDUCING ALIASING IN TDI BASED IMAGING, naming Andrew V. Hill and David Shortt as inventors, filed Aug. 8, 2012, application Ser. No. 13/569,607, which constitutes a regular (non-provisional) patent application of United States Provisional Patent Application entitled METHOD FOR REDUCING ALIASING IN TDI BASED IMAGING SYSTEMS, naming Andrew V. Hill and David Shortt as inventors, filed Aug. 8, 2011, Application Ser. No. 61/521,253. Each of the above applications is incorporated herein by reference in the entirety.

TECHNICAL FIELD

The present invention relates to integrated circuit manufacture and, more particularly, to time delayed imaging (TDI) based imaging systems for detecting defects in wafers used to manufacture integrated circuits.

BACKGROUND

Time delayed imaging (TDI) based imaging systems have been developed for detecting defects in wafers used to manufacture integrated circuits prior to printing and etching the desired circuit patterns on the wafers. In this type of imaging system, the wafer is conveyed (scanned) across the field of view of a TDI sensor, such as a Charge-Coupled Device (CCD) camera, which accumulates electric charge in proportion to gathered light reflected by the wafer while it is conveyed across the field of view of the camera. The camera includes an array of light gathering sensor elements, such as CCD elements, organized into a matrix of rows and columns. The elements of a particular row are electrically connected to each other so that the charge caused by the exposure is transferred from element to element along the row to integrate the charge generated by the elements of the row into a pixel reflecting the sum of the charge accumulated by the sensor elements of the row.

The TDI imaging process thereby causes the light gathered by a row of elements to be integrated (summed) over multiple sensor elements, resulting in a pixel that represents the light scattered by a particular region of the imaged wafer as that region is conveyed past multiple sensor elements. The process is then repeated for additional pixels to create a two-dimensional image of the wafer. Integrating the light reflected from a particular region of the wafer over an extended number of sensor elements in the scan direction increases the exposure from the corresponding region of the wafer, which aids in the imaging process by gathering a sufficient amount of light reflected from that region to assist in the detection of small defects, such as point defects in the wafer. This is particularly useful in darkfield imaging, where low levels of light are scattered by the wafer being imaged.

The orientation of the rows of the TDI sensor (referred to as the "sensor direction") is typically aligned with the direction of travel of the wafer being imaged as the wafer is conveyed across the field of view of the camera (referred to as the "scan direction"). In addition, the rate at which the accumulated charge is transferred along the sensor elements (referred to as the "sample clock rate") is synchronized with the rate at which the wafer is physically conveyed across the field of view of the sensor (referred to as the "scan rate"). Aligning the sensor direction with the scan direction and synchronizing the TDI sample clock rate with the wafer scan rate produces a digital image in which each pixel of the image corresponds to a particular, static region of the wafer as the image of that region is conveyed across a row of sensor elements.

In a conventional TDI wafer imaging system, the scan direction is carefully aligned with the sensor direction, and the sample clock rate is carefully set to match the physical scan rate of the wafer, so that the light gathered by a row of sensor elements is reflected from a particular, static region of the wafer as the wafer is conveyed across the field of view of the camera. This allows each pixel of the captured image to be precisely correlated with a specific physical region of the wafer under inspection, which allows small defects, such as point defects, to be picked up by the inspection system.

In TDI wafer imaging systems, it is often advantageous to increase the numerical aperture (NA) of the TDI sensor to increase the exposure of the TDI sensor to light scattered by the subject wafer. Increasing the exposure can be particularly useful when attempting to detect small defects, such as point defects, in darkfield optical configurations. It may also be desirable to increase the scan rate of the TDI system, which generally improves the speed of the inspection and thereby improves the overall cost of ownership of the inspection system. However, increasing the scan rate also has the effect of increasing the size of the region of the wafer corresponding to each pixel (pixel size) in the sampled image. Increasing both the NA and the pixel size can result in aliasing when the NA becomes high enough to allow image modulation at frequencies greater than $1/(2 \times \text{pixel size})$.

It would be desirable to image point defects at high numerical aperture while also sampling the image at high scan rates, resulting in relatively large pixel sizes, without introducing aliasing in the sampled images. This would enable greater capture of defect energy and higher-speed inspection while minimizing missed defects and false defects. However, the combined effect of increasing the numerical aperture while also increasing the effective pixel size can lead to unacceptable levels of aliasing, which corrupts the captured image and leads to lower defect capture rates and the detection of false defects.

There is, therefore, a continuing need for techniques for avoiding or counteracting the effect of aliasing when increasing the numerical aperture and effective pixel size in TDI imaging systems. More particularly, there is a need for effective anti-aliasing techniques for integrated circuit wafer inspection systems to improve the ability of the systems to capture low-signal defects, such as point defects in darkfield inspection systems, without sacrificing numerical aperture (exposure) or scan rate (pixel size).

SUMMARY

The invention may be embodied in a time delay integration (TDI) based wafer inspection system that introduces controlled blur into the sampled image to suppress spectral frequencies above the Nyquist frequency and thereby mitigate the occurrence of aliasing in the sampled image. Image blur may be introduced in the scan direction by desynchronizing the image motion (scan rate) from the charge transfer rate within the TDI sensor (sample clock rate). This desynchronization may be accomplished by altering the speed of wafer movement (changing the scan rate), altering the rate at which the TDI sensor transfers accumulated charge (changing the sample clock rate), or changing the magnification applied to the scanned image by the imaging optics prior to sampling. Image blur may be introduced in the cross-scan direction (orthogonal to the scan direction) by imparting a small alignment difference between the image scan direction and the TDI sensor direction. This alignment difference may be accomplished by changing the alignment of the wafer conveyor (changing the scan direction), changing the alignment of the TDI sensor (changing the sensor direction), or optically rotating the scanned image within the imaging optics prior to sampling.

To facilitate mitigation of aliasing in the scan direction, the wafer inspection system may be provided with adjustments for changing the speed of wafer movement, the TDI integration clock rate, and/or the magnification of the imaging optics. Alternatively or additionally, to facilitate mitigation of aliasing in the cross-scan direction, the wafer inspection system may be provided with adjustments for changing the alignment of the wafer conveyor, the alignment of the TDI sensor, or rotating the scanned image within the imaging optics. For example, the TDI sensor and/or the wafer conveyor may be mounted on a swivel to allow adjustment of the alignment of the image scan direction with respect to the alignment of the sensor. The imaging optics may also include one or more adjustable mirrors or prisms to rotate the scanned image prior to sampling by the TDI sensor. The controllable parameters may be adjusted manually or automatically by a computer control system to detect and mitigate aliasing prior to scanning and sampling the wafers for defect detection. The computer control system may incorporate a feedback loop to automatically implement the anti-aliasing techniques in a priority order as part of a calibration procedure prior to using the inspection to sample wafers for defect detection.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE FIGURES

The numerous advantages of the invention may be better understood with reference to the accompanying figures in which.

DETAILED DESCRIPTION

The invention may be embodied in a time delay integration (TDI) based wafer inspection system used to detect defects in wafers used to manufacture integrated circuits. Although the preferred embodiments described below relate to TDI based wafer inspection system, the invention is not limited to wafer inspection systems and it will be understood that the anti-aliasing techniques of the invention may also be applied to other TDI inspection systems, such as TDI based inspection systems for photomasks, solar cells, hard disk substrates, and so forth.

In general, aliasing is caused by high spectral frequencies that exceed the Nyquist rate, which is a function of the pixel size and the numerical aperture (NA) of the camera. The invention introduces controlled "blur" into the sampled image to suppress spectral frequencies above the Nyquist rate and thereby mitigate the occurrence of aliasing in the sampled image. In this manner, the invention allows a TDI based wafer inspection system to utilize higher numerical aperture-to-pixel size ratios than have previously been achievable due to aliasing limitations. This capability is particularly useful for achieving good defect sensitivity at high scan rates in darkfield imaging systems. While the invention is particularly adept at picking up small defects, such as point defects, in darkfield imaging, it will be appreciated that this is but on example use of the invention, which is generally applicable to detecting all types of wafer defects in darkfield, brightfield and other any other wafer imaging configuration.

Aliasing can be mitigated through the introduction of controlled blur into the sampled image to suppress the high frequency components in the captured image. In the present invention, controlled blur is introduced in the scan direction ("X" direction in the mathematics) of the TDI inspection system by desynchronizing the image motion (scan rate) from the charge transfer rate within the TDI sensor (sample clock rate). That is, aliasing in the scan direction can be mitigated by any mechanism that effectively changes the image scan rate with respect to the TDI sample clock rate. For example, blur in the scan direction can be intentionally introduced in at least three ways: the TDI sample clock rate can be increased or decreased (change the sample clock rate); the scanning speed of the wafer conveyor can be increased or decreased (change the scan rate); or the magnification of the imaging optics can be increased or decreased. In each case, a slight mismatch is created between the wafer scan rate and TDI sample clock rate.

In addition or as an alternative, image blur may be introduced in the cross-scan direction (orthogonal to the scan direction, "Y" direction in the mathematics), by imparting a small difference in the alignment between the direction of image motion (scan direction) and the direction that charges transfer within the TDI sensor (sensor direction). Blur in the cross-scan direction can be intentionally introduced by physically rotating the wafer conveyor (change the scan direction), by physically rotating the TDI sensor (change the sensor direction), or by optically rotating the scanned image within the imaging optics prior to sampling. For example, aliasing mitigation in the cross-scan direction can be implemented by placing the TDI sensor and/or the wafer conveyor on swivel that allows the TDI sensor or and/or the wafer to be rotated by small, controlled angles about the optical axis. The wafer image can also be rotated optically through a combination of steering mirrors or prisms within the imaging optics. The orientation of one or more of the steering mirrors or prisms may be adjustable to allow the amount of image rotation to be adjusted, as desired.

Increasing the numeric aperture (NA) of the imaging system increases the amount of light captured from a small defect, such as a point defect, particularly when inspecting in a darkfield optical configuration. Increasing the area of the wafer that each pixel represents generally improves the speed of the inspection and thereby improves the overall cost of ownership of the inspection system. However, these two trends—increasing the NA and increasing the effective pixel size—can also lead to aliasing in the image. Aliasing in wafer defect inspection is undesirable because it can lead to lower defect capture rates and the detection of false defects.

It is therefore desirable to image point defects at relatively high-NA while acquiring image data from the wafer with the sensor matrix (sampling the wafer image) at relatively high scan rates (relatively large pixel sizes), without introducing aliasing effects. This enables greater capture of defect energy and higher-speed inspection while minimizing missed defects and false defects. In prior TDI inspection systems, aliasing effects have been mitigated by low-pass filtering the image after it has been sampled (pixilated). Once an image is sampled, however, aliasing cannot be effectively eliminated without significant adverse effects. In particular, digital filtering after the image has been sampled can reduce the aliasing effects, but it does so with a severe penalty to image resolution and contrast because aliased frequencies are spread throughout the sampled frequency range. Defocusing the image prior to sampling can also reduce aliasing effects, but when imaging objects such as integrated circuit wafers with 3-dimensional depth, the anti-aliasing effect produced by defocusing may vary across the image, and defocusing may produce other unwanted side effects such as focusing on an undesired depth region.

Prior image anti-aliasing techniques involving blurring of the scanned image prior to sampling include the intentional introduction of defocus or the introduction of a blurring optical element in the image path. Ground glass, diffractive optical elements and birefringent plates are all examples of blurring optical elements that have been introduced into the imaging optics to reduce aliasing effects. However, defocusing and the introduction of a blurring element into the imaging optics also have the negative effects of increasing the ringing or side-lobes in the point spread function (PSF) of the optical system. Ringing is undesirable in wafer defect inspection, since it leads to bright areas of the image (for example page break regions) contributing light to the dark areas (for example array regions). This in turn reduces the image contrast of the dark areas and makes defect detection more difficult.

The present invention, on the other hand, implements anti-aliasing techniques to blur the image so that the high-frequency content is suppressed before the image is sampled and without defocusing the image. A TDI sensor produces the sharpest image when the image moves in exactly the same direction (scan direction) that the charges represented in the pixels are transferred along the rows of sensor elements (sensor direction) and when the image moves at the same rate (scan rate) as the charges are transferred along the rows of TDI sensor elements (sample clock rate). If the charges in the sensor elements are transferred slower or faster than the image is moving, then with each charge transfer step the additional accumulation of charge on a pixel will come from a slightly different physical location on the wafer that is offset in the scan direction ("X" direction). This effectively blurs the final image acquired by the TDI sensor in the scan direction.

If the TDI sensor is rotated by a relatively small angle about the optical axis, then with each charge transfer step the additional accumulation of charge reflected in a pixel will come from a physical location on the wafer that is offset primarily in the cross-scan direction. This effectively blurs the final image acquired by the TDI in the cross-scan direction ("Y" direction). By desynchronizing the scan rate from the sample clock rate, and by altering the alignment of the scan direction with respect to the sensor direction, blur can be introduced into the sampled image in both the scan and cross-scan directions independently and in a well-controlled manner. It should also be noted that this technique allows for continuous adjustment of the amount of the blur over a wide range of values, making the invention applicable over a wide range of pixel sizes, NA values, and wafer/defect types. In addition, the invention may be applied in iterations and through multiple applications of controlled blur in the scan or cross-scan directions, and desired. This is in addition to the controlled blur being "X" and "Y" independent, well-controlled, and optionally automatically controlled, in each direction.

The intentional, controlled introduction of blur into the sampled image has the effect of reducing the high spatial frequency content of the captured image, thereby mitigating the aliasing effect experienced with a nominal configuration in which the scan rate is precisely synchronized with the sample clock rate and the scan direction is precisely aligned with the sensor direction. The resolution of the captured image is correspondingly decreased slightly by the blurring in that the pixel size is somewhat extended or compressed in comparison to the nominal situation. But this slight loss in resolution is more than recovered through suppression of the aliasing effect, which is accomplished more effectively, and with less severe tradeoffs, than the post-capture digital filtering techniques used previously.

Through these pre-sampling anti-aliasing techniques, the invention produces a number of advantages over existing anti-aliasing techniques. Specifically, ringing in the PSF is not increased and additional optical elements are not required to introduce blur. In addition, the degree of suppression of high spatial frequencies can be readily adjusted, which is not possible with ground glass and other blur inducing optical elements that introduce a fixed amount of blur into the sampled image. Furthermore, the amount of suppression of high spatial frequencies produced by the present invention is consistent across the entire image and independent control can be provided for the anti-aliasing effects in both the scan and cross-scan directions.

It should also be understood that all of the adjustment mechanisms described above need not be provided in a practical embodiment, particularly in view of the fact that multiple techniques are described for imparting the controlled blurring in each direction. One mechanism per direction will likely be considered sufficient in practice. For example, adjusting the magnification and optical rotation through adjustments in the imaging optics may be preferred when these adjustments are provides as part of the imaging optics as original product features. If optical adjustments are not available, electronic control of the TDI sample clock rate may be the most cost effective approach when the camera comes with clock rate adjustment as original product features. For inspection systems without available optical or clock rate adjustments, adjustment of the physical speed wafer conveyor and adjustment of the orientation of the wafer conveyor with respect to the TDI sensor may be the most practical approach.

Figure 1A:
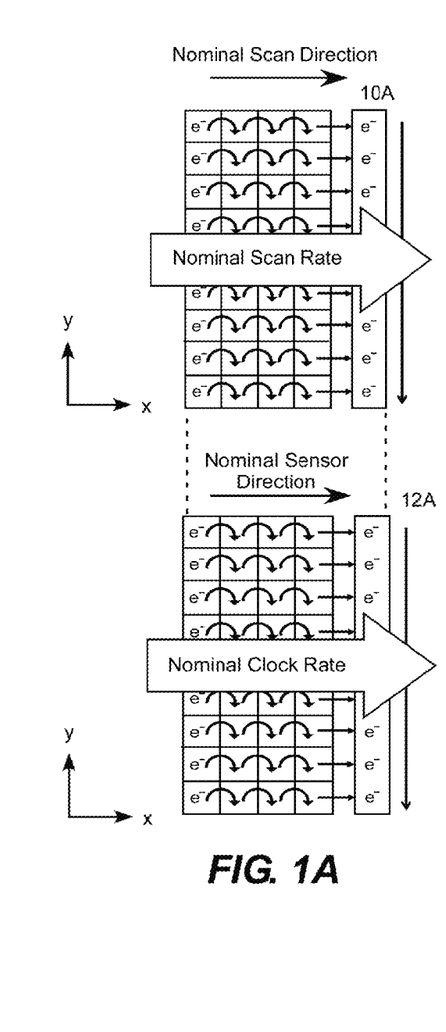
FIGS. 1A-1C show a conceptual illustration of an anti-aliasing technique for a wafer inspection system including the introduction of controlled blur in the scan direction through a time integration offset.
Figure 1B:
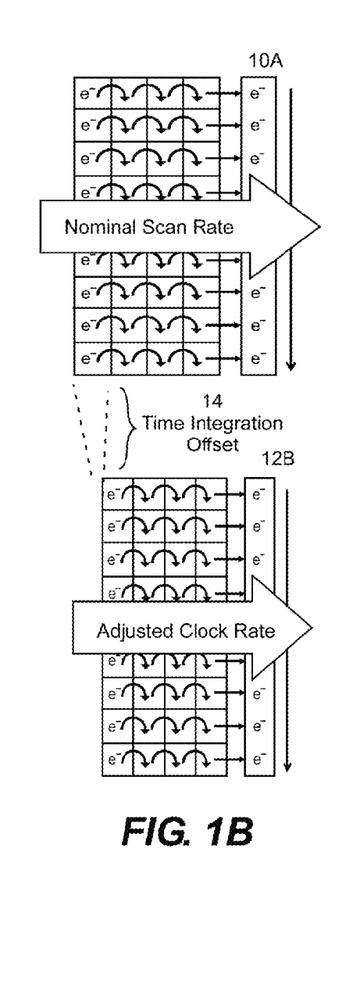
Figure 1C:
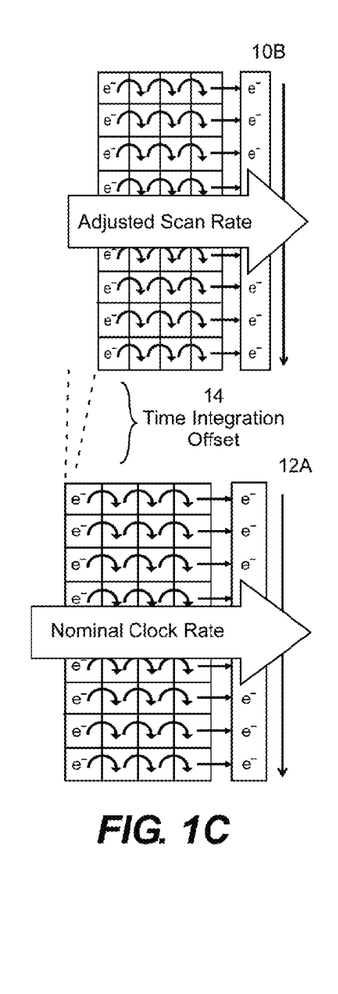

FIGS. 1A-1C show a conceptual illustration of an alias mitigation technique involving the introduction of controlled blur in the scan direction through a time integration offset 14. A coordinate system shows the "X" direction (scan direction) and the "Y" direction (cross-scan direction) for reference in the following system description and the subsequent mathematical development. To set the nomenclature, a wafer conveyor moves the wafer in the scan direction across the field of view of the TDI sensor at the scan rate. The TDI sensor includes a number of rows of sensor elements extending in the sensor direction. The charge generated in proportion to light captured by the sensor elements of a row is transferred from element to element along the row to integrate the signal generated by the elements of the row into integrated pixel. The rate at which the charge is conveyed from element to element along the rows of sensor elements is controlled by the sample clock rate of the TDI sensor.

In the "nominal" TDI configuration without any of the controlled blur anti-aliasing techniques of the present invention, the sample clock rate is precisely synchronized with the scan rate and the sensor direction is precisely aligned in the scan direction. More specifically, FIG. 1A shows the nominal image capture situation with the matrix 10A depicting image scanning caused by motion of the wafer across the field of view of the TDI sensor. For descriptive convenience, in the nominal configuration, the wafer is defined as moving across the TDI sensor in a nominal scan direction at a nominal scan rate. The matrix 12A depicts image capture by the TDI sensor. The image is defined as being sampled at the nominal sample clock rate with the rows of the sensor aligned in the nominal sensor direction. In addition, the imaging optics between the wafer location and the location of the TDI sensor are set to a nominal magnification, which controls the cross-scan size of the region of the wafer corresponding to the field of view of the TDI sensor. This sets the nominal pixel size in the cross-scan direction. The magnification in combination with the scan rate controls pixel size in the scan direction.

In the nominal configuration shown in FIG. 1A, the nominal scan direction is carefully aligned with the nominal sensor direction, the nominal scan rate is carefully synchronized with the nominal sample clock rate, and the nominal magnification is carefully set so that each pixel created by the TDI sensor corresponds to a static region of the wafer having equal size in the scan and cross-scan directions. This configuration represents the fully calibrated "base case" to which the various adjustments described in the disclosure are applied to impart desired anti-aliasing effects. As noted previously, increasing the numerical aperture (NA) of the TDI sensor increases the exposure of the sensor to light scattered by the wafer. In addition, increasing the scan rate increases the pixel size of the region of the wafer corresponding to each pixel. Increasing the NA while also increasing the pixel size by increasing the scan rate results in aliasing in the sampled image when the NA becomes high enough to allow image modulation at frequencies greater than $1/(2 \times pixel\ size)$. The present invention provides techniques for suppressing the aliasing without having to reduce the NA or the pixel size.

FIG. 1B is a conceptual illustration of an anti-aliasing technique in which blur is introduced in the scan direction ("X" Direction in the figure) by desynchronizing the scan rate from the sample clock rate. If the scan rate matches the TDI sample clock rate precisely, the integrated sum reflected in each pixel corresponds to a static portion of the physical wafer in the scan direction. If, on the other hand, there is a slight mismatch between the scan rate and the sample clock rate, the integrated sum represented by the pixel corresponds to an extended or contracted portion of the physical wafer in the scan direction. In FIG. 1B, the matrix 10A illustrates scan rate, which in this example is same as the nominal scan rate shown in FIG. 1A. The matrix 12B illustrates the sample clock rate, which has been adjusted from the nominal sample clock rate to desynchronize the sample clock rate from the scan rate. This mismatch is represented by the time integration offset 14. The offset blurs the image in the scan direction in that the pixel captured by a row of the TDI sensor corresponds to an extended or contracted region of the subject wafer in the scan direction.

The effect of blurring in the scan direction can also be accomplished by altering the physical scan rate of the wafer rather than adjusting the clock rate of the TDI sensor. This alternative is illustrated by FIG. 1C, in which the matrix 12A represents the same nominal clock rate shown in FIG. 1A, while the matrix 10B represents an adjusted scan rate producing an equivalent time integration offset 14. Both techniques, scan rate adjustment and clock rate adjustment, could be utilized separately or in combination if desired.

Figure 2:
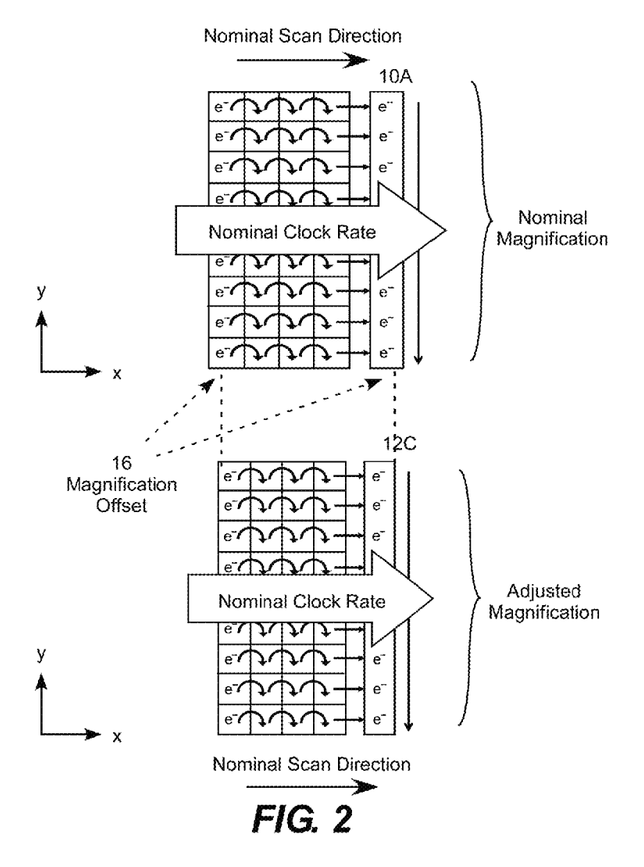
FIG. 2 is a conceptual illustration of an anti-aliasing technique for a wafer inspection system including the introduction of controlled blur in the scan direction through a magnification offset.

FIG. 2 is a conceptual illustration of another alias mitigation technique using controlled blur in the scan direction, in this case the introduction of magnification offset 16. The matrix 10A illustrates the nominal scan rate shown in FIG. 1A. The matrix 12C reflects the nominal clock rate, but the magnification applied by the image optics has been altered from the nominal magnification to change the size of the sampled image with respect to the physical region of the wafer. This alteration in magnification produces a mismatch in the scan direction because the reduced size image effectively moves across the field of view of the TDI sensor faster than the TDI sample clock rate. This mismatch in the scan direction is represented by the magnification offset 16, which is similar to the effect produced by a mismatch between the scan rate and the TDI sample clock rate shown in FIGS. 1A-1C.

Figure 3:
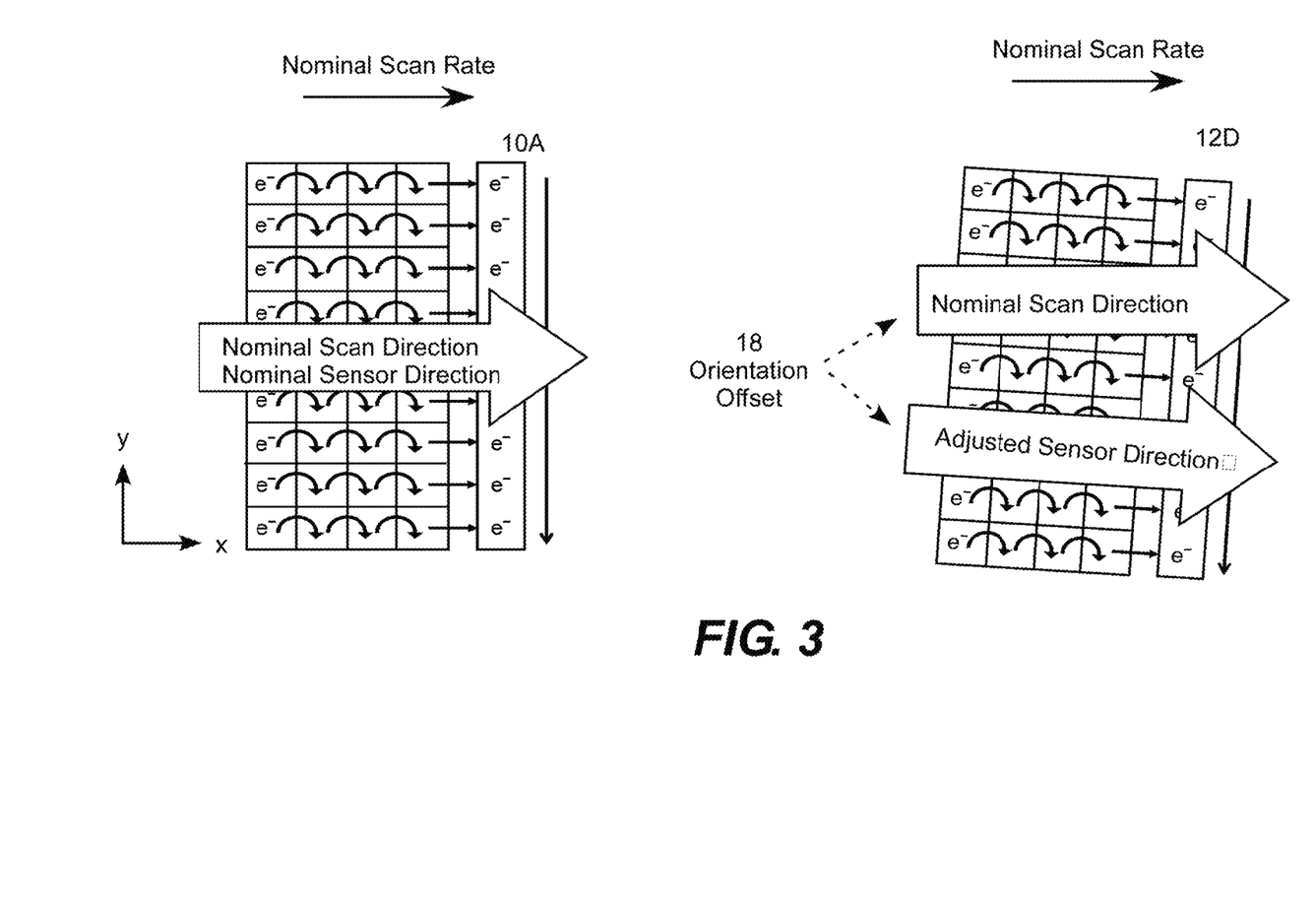
FIG. 3 is a conceptual illustration of an anti-aliasing technique for a wafer inspection system including the introduction controlled blur in the cross-scan through an orientation offset.

FIG. 3 is a conceptual illustration of alias mitigation in the cross-scan direction through the introduction of an orientation offset 18 between the scan direction and the sensor direction. If the scan direction matches the sensor direction precisely, the integrated sum reflected in each pixel corresponds to a static portion of the physical wafer in the cross-scan direction. If, on the other hand, there is a slight mismatch between the scan direction and the sensor direction, the integrated sum represented by the pixel corresponds to an extended or contracted portion of the physical wafer in the cross-scan direction. The matrix 10A illustrates the nominal configuration in which the scan direction is aligned with the sensor direction. To impart the controlled blur in the cross-scan direction, the matrix 10B illustrates a difference between the scan direction and the sensor direction. This mismatch is represented by the orientation offset 16, which blurs the image in the cross-scan direction.

In the example shown in FIG. 3, the scan direction is nominal and the sensor direction has been altered slightly. Alternatively, the sensor direction could remain nominal and the scan direction could be altered slightly to achieve the same anti-alias effect. It should also be noted that the orientation offset also creates a slight blur in the scan direction, but this effect is less pronounced in the scan direction due to integration of the signal.

Figure 4:
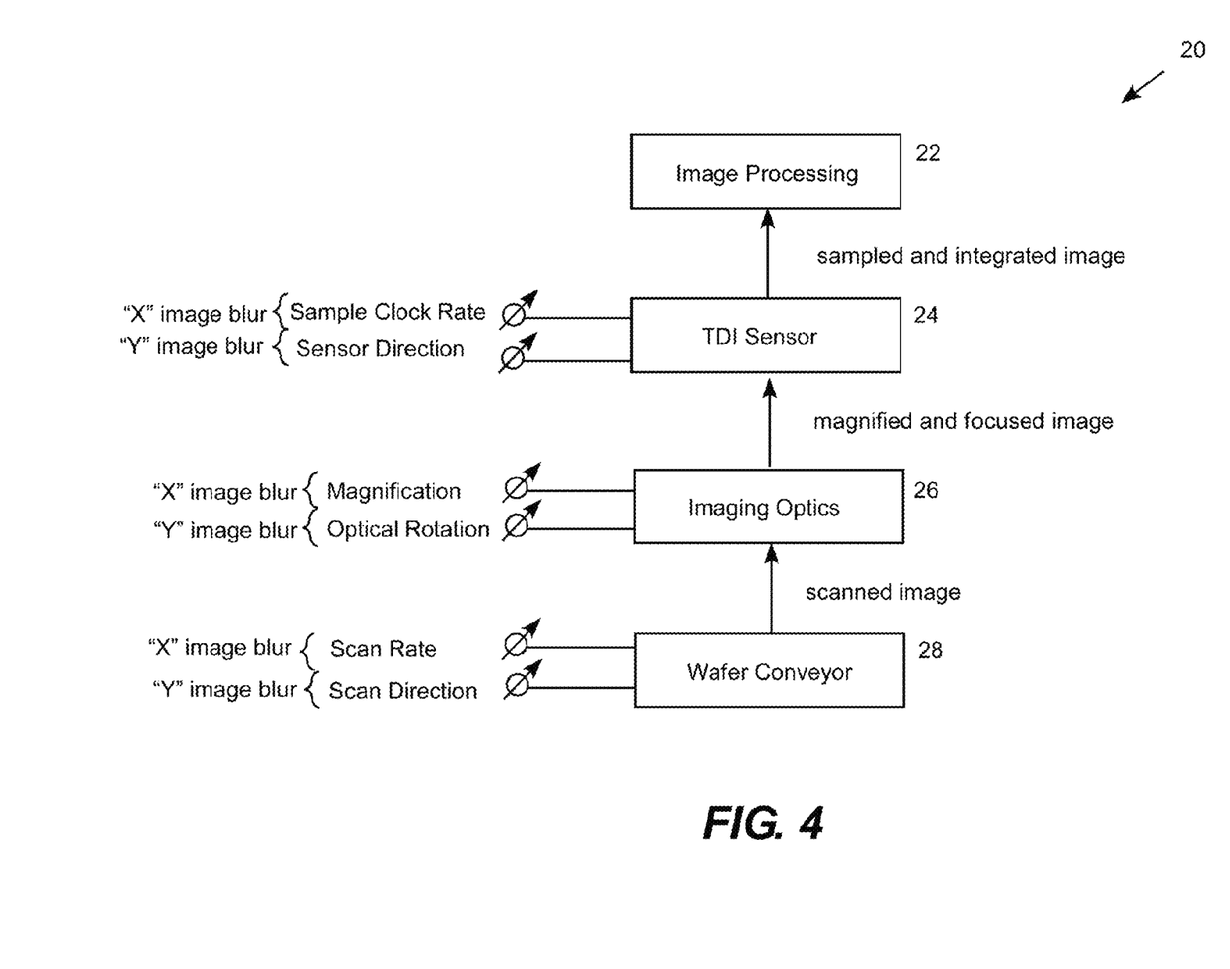
FIG. 4 is a block of a wafer inspection system including an anti-aliasing system.

FIG. 4 is a block diagram of a wafer inspection system 20 incorporating the anti-aliasing techniques of the present invention. An image processing system 22 performs defect detection based on the integrated pixilated image produced by the TDI sensor 24 and may also perform other image processing operations unrelated to the present invention. Imaging optics 26 are located between the TDI sensor 24 and a wafer conveyor 28, which moves the wafer being imaged across the field of view of the sensor. As explained previously, the controlled blur in the scan direction is imparted by created a mismatch between the scan rate and the TDI sample clock rate, whereas the controlled blur in the cross-scan direction is imparted by created a mismatch between the scan direction and the sensor direction.

The techniques for creating the mismatch between the scan rate and the sample clock rate include adjusting the integration clock rate of the TDI sensor 24, adjusting the physical scan rate of the wafer conveyor 28, and adjusting the magnification applied by the imaging optics 26. The techniques for imparting the mismatch between the scan direction and the sensor direction include changing the physical alignment of the TDI sensor 24, changing the physical alignment of the wafer conveyor 28, and rotating the optical image with a system of prisms and mirrors within the imaging optics 26 prior to sampling.

In practice, the adjustable parameters described above may be manipulated manually. For example, the TDI sensor may be mounted on a swivel and a technician may manually rotate the sensor to adjust its orientation. Similarly, the wafer conveyor may be mounted on a swivel to allow a technician to manually rotate the conveyor to adjust its orientation. In addition, the TDI sensor may be provided with a manual TDI sample clock rate knob so that a technician can manually adjust the knob to change the TDI sample clock rate. The wafer conveyor could also be provided with a manual speed knob to allow a technician to manually adjust the knob to change the wafer scan rate. The imaging optics could also be provided with a manual magnification knob so that a technician can manually adjust the knob to change the image magnification. Similarly, the imaging optics might also be provided with an image rotation knob allowing a technician to change the alignment of a prism or mirror within the imaging optics to optically rotate the image.

Figure 5:
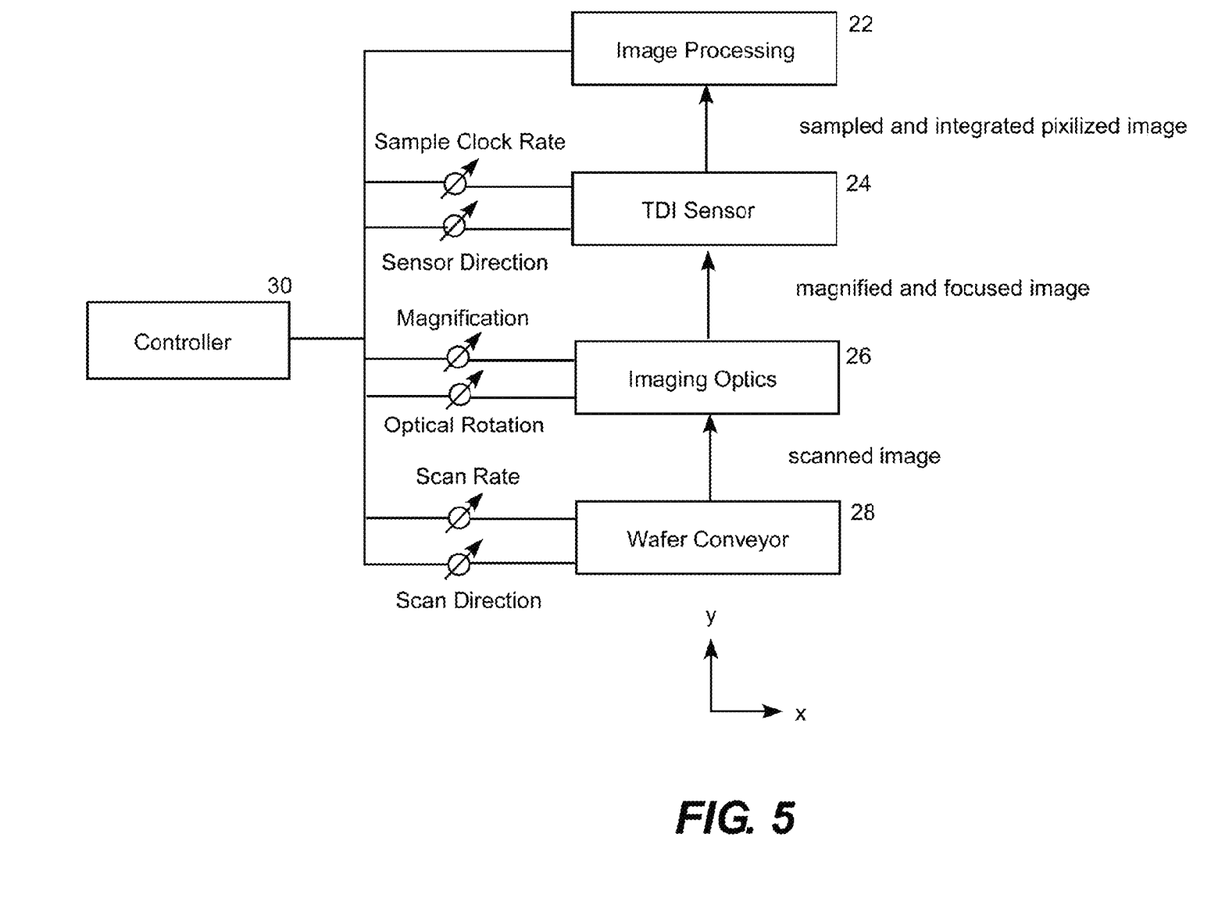
FIG. 5 is a block of a wafer inspection system including a computer controlled anti-aliasing system.

FIG. 5 illustrates a semi- or fully-automated anti-aliasing system in which one or more of the various adjustment mechanisms described above are under the control of a computer controller 30. In this embodiment, motors may be utilized to implement the various adjustments under the control of the computer to mitigate any aliasing detected in the sampled image. Various control schemes may be utilized to implement the various adjustments in a prioritized manner, which may include but are not limited to automatic feedback control schemes.

Figure 6:
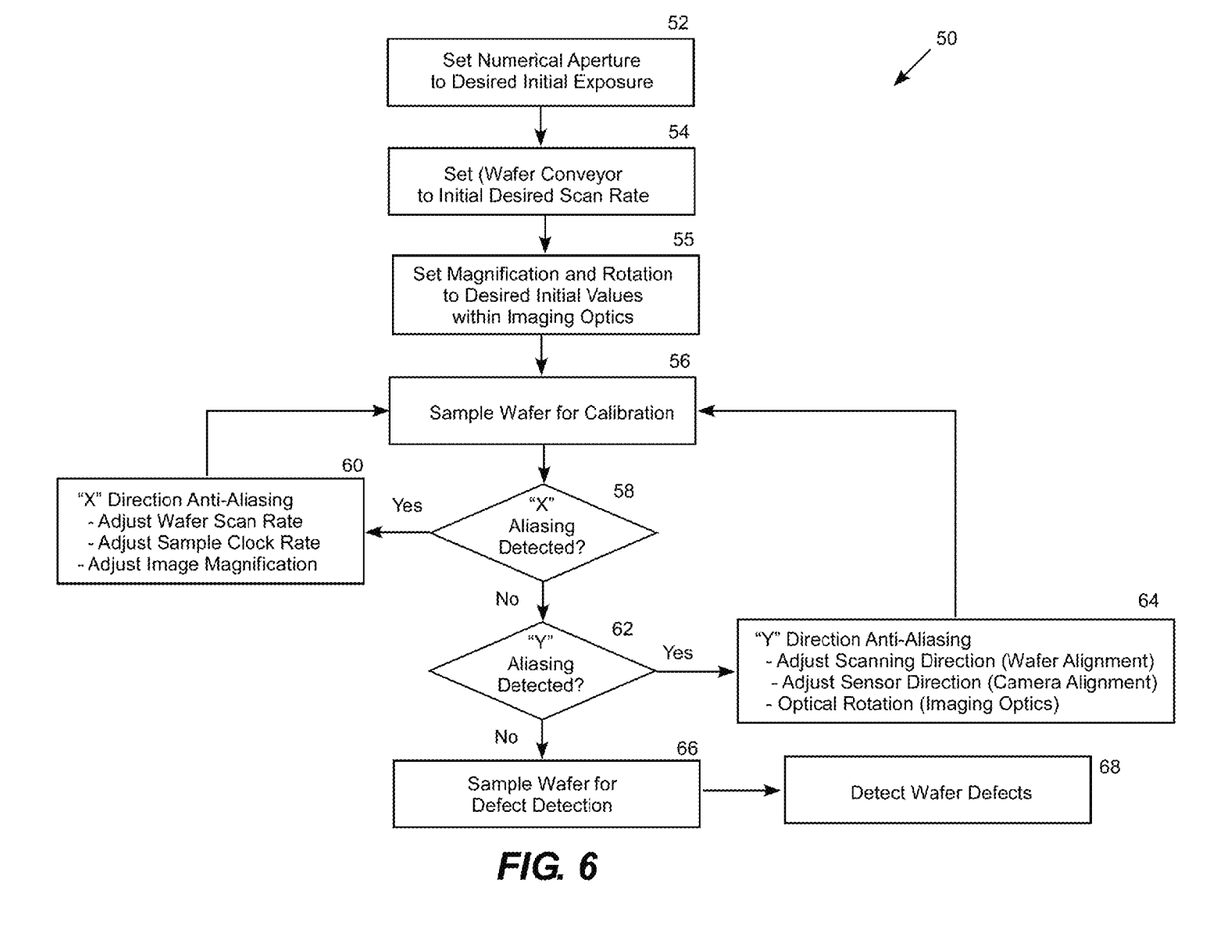
FIG. 6 is a logic flow diagram for mitigating aliasing in a wafer inspection system.

FIG. 6 is a logic flow diagram illustrating routine 50, which is a simplified example of an anti-aliasing control scheme. This routine merely provides one example to illustrate an embodiment of the invention, which is not limited to the specific control scheme described for the illustrative embodiment. In step 52, the numerical aperture is set to a desired initial exposure. Step 52 is followed by step 54, in which wafer conveyor is set to a desired initial scan rate. Step 54 is followed by step 55, in which the magnification and optical rotation are set to desired initial values within the imaging optics. Step 55 is followed by step 56, in which controller receives a sampled image for calibration. Step 56 is followed by step 58, in which the controller determines whether aliasing is detected in the scan direction ("X" direction). It should be noted that a minimal level of aliasing may be tolerated, and step 58 should be understood to encompass determining whether the aliasing is below a threshold or meets other criteria indicating that the imaging process may continue.

If aliasing is detected in the scan direction, the "Yes" branch is followed from step 58 to step 60, in which the aliasing is mitigated in the scan direction. In particular, the wafer scan rate may be adjusted, the sample clock rate may be adjusted, and/or the magnification of the imaging optics may be adjusted. All of these parameters need not be adjustable, and the controller may select among the available adjustments in any suitable manner. Following scan direction alias mitigation in step 60, routine 50 loops back to step 56, in which the wafer is sampled again for calibration. It should be understood that the loop back may be eliminated if iterative adjustment is not desired.

If aliasing is not detected in the scan direction ("X" direction), the "No" branch is followed from step 58 to step 62, in which the controller determines whether aliasing is detected on the cross-scan direction ("Y" direction). If aliasing is detected in the cross-scan direction, the "Yes" branch is followed from step 62 to step 64, in which the aliasing is mitigated in the cross-scan direction. In particular, the wafer scan orientation may be adjusted, the alignment of the TDI sensor may be adjusted, or the image may be optically rotated with the imaging optics. All of these adjustments need not be provided and the controller may select among them in any suitable manner. Again, a minimal level of aliasing may be tolerated, and step 64 should be understood to encompass determining whether the aliasing is below a threshold or meets other criteria indicating that the imaging process may continue. Following cross-scan direction alias mitigation in step 64, routine 50 loops back to step 56, in which the wafer is sampled again for calibration. It should again be understood that the loop back may be eliminated if iterative adjustment is not desired.

If aliasing is not detected in the cross-scan direction, the anti-aliasing techniques are complete and step 62 is followed by step 66, in which the wafer is scanned and sampled for defect detection. Step 66 is followed by step 68, in which the image processing system performs defect detection and may also perform other image processing operations unrelated to the present invention.

It should also be understood that all of the adjustment mechanisms described above need not be provided in a practical embodiment, particularly in view of the fact that multiple techniques are described for imparting the controlled blurring in each direction. One mechanism per direction will likely be considered sufficient in practice. For example, adjusting the magnification and optical rotation through adjustments in the imaging optics 26 may be preferred when these adjustments are provides as part of the imaging optics as original product features. If optical adjustments are not available, electronic control of the TDI sample clock rate may be the most cost effective approach when the camera comes with clock rate adjustment as original product features. For inspection systems without available optical or clock rate adjustments, adjustment of the physical speed wafer conveyor and orientation of the wafer conveyor ro rhgw TDI sensor may be the most practical approach.

Turning to a mathematical development supporting the efficacy of the invention, a one-dimensional image can be represented in the spatial frequency domain by the following optical modulation transfer function MTF:

$$MTF_{Optical} = \frac{2}{\pi}\left[\cos^{-1}\left(\frac{f\lambda}{2NA}\right) - \frac{f\lambda}{2NA}\sqrt{1-\left(\frac{f\lambda}{2NA}\right)^2}\right] \quad \text{Eq. 1}$$

Aliasing occurs when the numerical aperture (NA) is high enough to allow image modulation at frequencies greater than 1/(2×pixel size). A square pixel samples the image as a rectangular function:

$$\Pi(x/s) \quad \text{Eq. 2}$$

where s is the pixel width. In the frequency domain, the pixel sampling MTF can be expressed as:

$$\text{sinc}(sf) \text{ or } \sin(\pi sf)/(\pi sf) \quad \text{Eq. 3}$$

Figure 7:
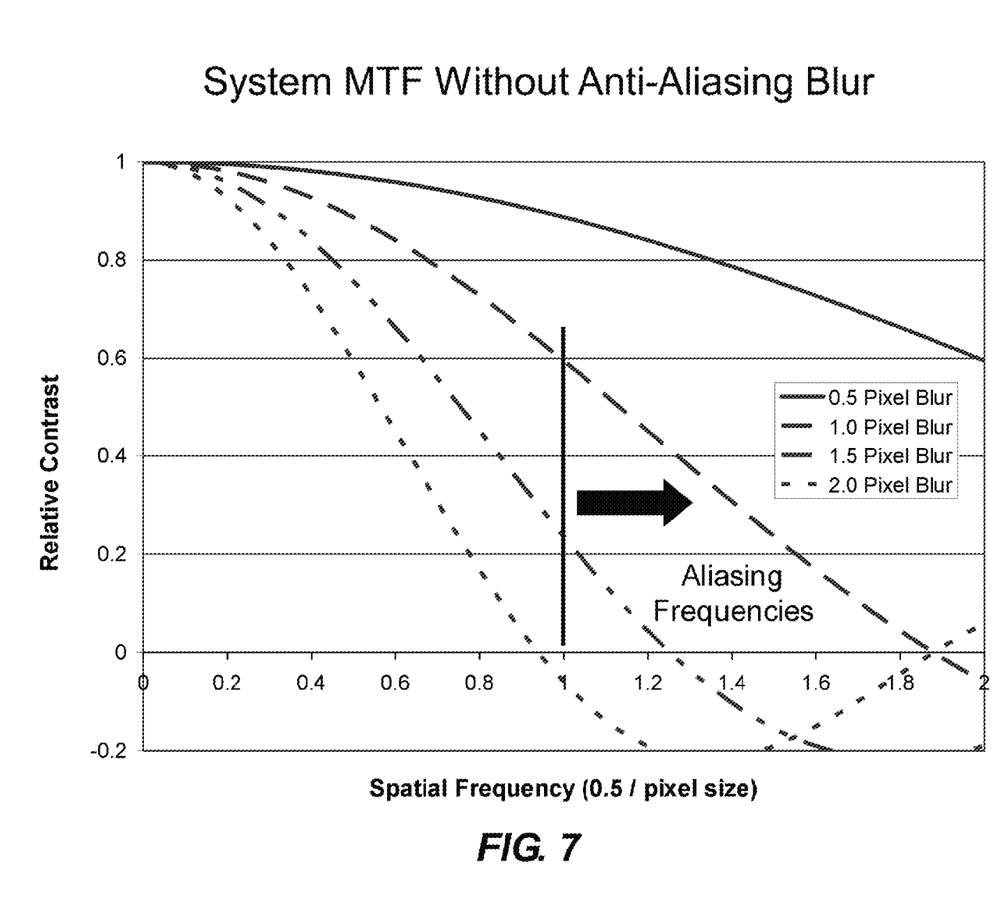
FIG. 7 is graph illustrating aliasing occurring in a wafer inspection system without the anti-aliasing effect of controlled blur.

The product of the optical MTF and the sampling MTF represents the overall MTF for a pixelating imaging system. FIG. 7 is a graph illustrating aliasing occurring at example pixel sizes relative to the spatial imaging frequency. The high level of aliasing is reflected in the large portion of the transfer functions above (to the right of) the aliasing frequency shown on the graph. Note that the sampling MTF reduces modulation in frequencies that suffer aliasing, those frequencies greater than 1/(2×pixel size), but does not eliminate the modulation. The invention provides techniques for introducing additional blurring to further dampen the high frequency modulation.

Blur in the sampled image can be introduced in the "X" direction (scan direction) by de-synchronizing the image motion relative to the charge clocking and in the "Y" direction (cross-scan direction) by rotating the image prior to sampling by the TDI sensor.

$$\text{Blur}(x) = \Delta_{E/N}(x) \cdot \prod\left(\frac{x}{E}\right) \quad \text{Eq. 4}$$

Where E is the total x-delay or y-shift in the image from when it is sampled by the first pixel to when it is sampled in the last pixels in the TDI row, and N is the number of pixels in the TDI row. The MTF of the TDI induced blur is then given by:

$$MTF_{Blur}(f) = \Delta_{N/E}(f) \otimes \frac{\sin(\pi Ef)}{\pi Ef} \quad \text{Eq. 5}$$

The sampled and blurred image is given by:

$$I(x) \otimes \Pi(x/s) \otimes [\Delta_{E/N}(x) \cdot \Pi(x/E)] \quad \text{Eq. 6}$$

The system MTF including the blur is the given by:

$$MTF_{Optical} \cdot \frac{\sin(\pi sf)}{\pi sf} \cdot \left[\Delta_{N/E}(f) \otimes \frac{\sin(\pi Ef)}{\pi Ef}\right] \quad \text{Eq. 7}$$

Figure 8:
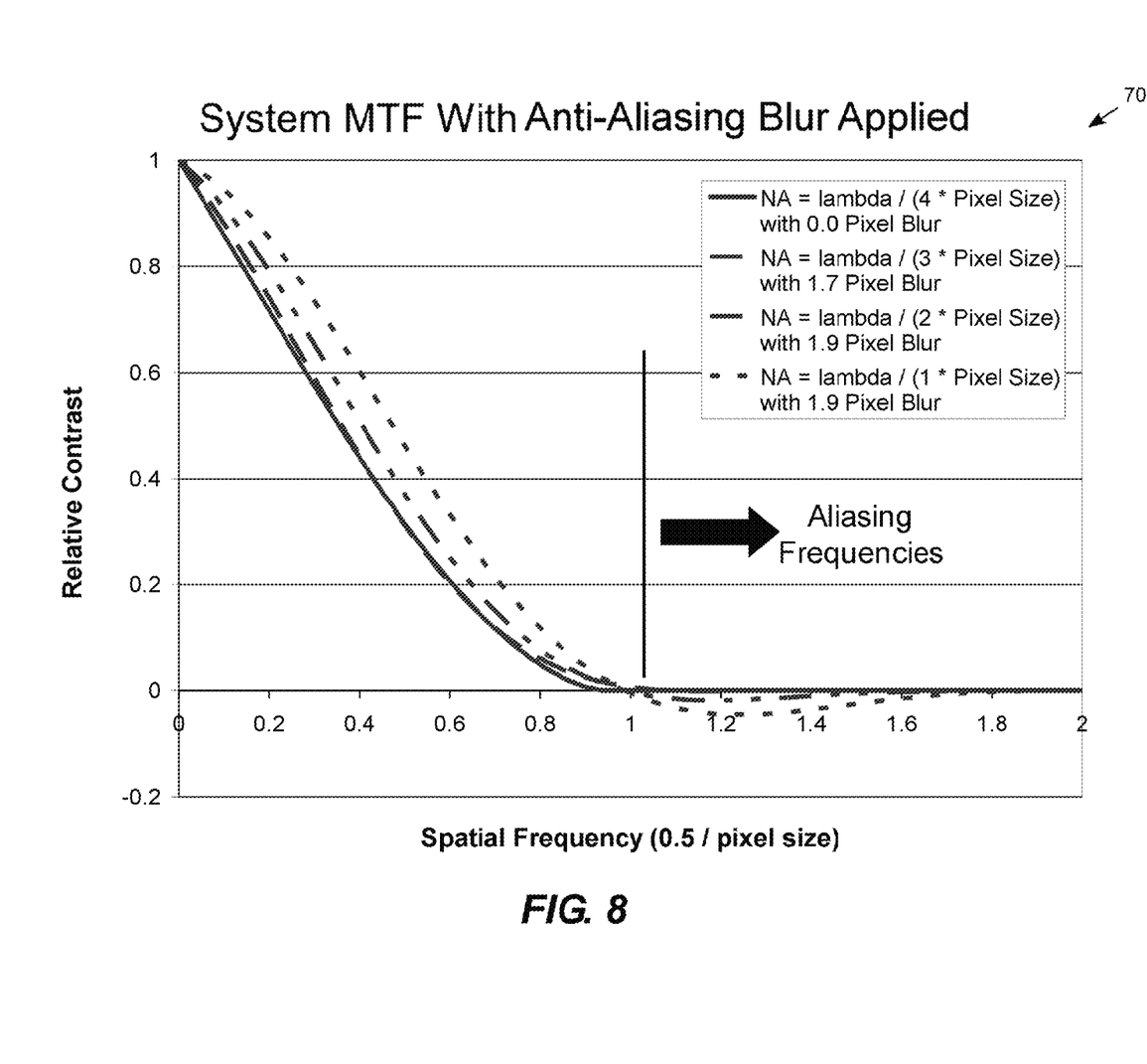
FIG. 8 is graph illustrating the mitigation of aliasing in the inspection system through the introduction of controlled blur.

FIG. 8 is a graph 70 showing the system MTF after TDI blur anti-aliasing has been applied for various numerical aperture settings. The amount of blur is set at each NA to minimize the image modulation at frequencies greater than 1/(2×pixel size). Comparing FIG. 8 to FIG. 7 demonstrates the effectiveness of the controlled blurring techniques in reducing the effect of aliasing, which is reflected in the graphs by the much larger portion of the transfer functions occurring below (to the left of) the aliasing frequency after blur anti-aliasing has been applied.

The present invention may consist (but not required to consist) of adapting or reconfiguring presently existing systems. Alternatively, original equipment may be provided embodying the invention.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A wafer inspection system for suppressing aliasing comprising:
    imaging optics configured to at least magnify a scanned image of a wafer, the scanned image acquired along a scan direction;
    a time integration delay sensor comprising one or more sensor elements arranged in a matrix extending along one or more sensor directions, the matrix including a set of columns and a set or rows, the time integration delay sensor configured to:
        acquire image data from the at least magnified scanned image with the sensor matrix at a selected sample clock rate;
        generate integrated image data with the acquired image data; and
        generate a pixilated image of the wafer from the integrated image data, wherein at least some pixels of the pixilated image correspond to a region of the wafer;
    an image processor configured to analyze the pixilated image to detect wafer defects; and
    an anti-aliasing system configured to desynchronize a scan rate of the wafer from the selected sample clock rate to blur the image data in the scan direction.

2. The wafer inspection system of claim 1, wherein the anti-aliasing system is configured to adjust the selected sample clock rate of the time integration delay sensor.

3. The wafer inspection system of claim 1, wherein the anti-aliasing system is configured to adjust the scan rate of the wafer.

4. The wafer inspection system of claim 1, wherein the anti-aliasing system is configured to adjust the magnification applied by the imaging optics.

5. The wafer inspection system of claim 1, wherein the anti-aliasing system is configured to desynchronize the scan rate of the wafer from the selected sample clock rate in response to a user input.

6. The wafer inspection system of claim 1, wherein the anti-aliasing equipment further comprises:
    a controller configured to desynchronize the scan rate of the wafer from the selected sample clock rate.

7. A wafer inspection system configured for suppressing aliasing comprising:
    imaging optics configured to at least magnify a scanned image of a wafer, the scanned image acquired along a scan direction;
    a time integration delay sensor comprising one or more sensor elements arranged in a matrix extending along one or more sensor directions, the matrix including a set of columns and a set of rows, the time integration delay sensor configured to:
        acquire image data from the at least magnified scanned image with the sensor matrix at a selected sample clock rate;
        generate integrated image data with the acquired image data; and
        generate a pixilated image of the wafer from the integrated image data, wherein at least some pixels of the pixilated image correspond to a region of the wafer;
    an image processor configured to analyze the pixilated image to detect wafer defects; and
    an anti-aliasing system configured to adjust alignment of the scan direction with respect to a sensor direction to blur the image data in a cross-scan direction, the cross-scan direction being orthogonal to the scan direction.

8. The wafer inspection system of claim 7, wherein the anti-aliasing system is configured to adjust the alignment of the time integration delay sensor.

9. The wafer inspection system of claim 7, wherein the anti-aliasing system is configured to adjust the alignment of a wafer conveyor, the wafer conveyor configured to translate the wafer across a field of view at a scan rate along the scan direction to create the scanned image of the wafer.

10. The wafer inspection system of claim 7, wherein the anti-aliasing system is configured to optically rotate the scanned image prior to sampling.

11. The wafer inspection system of claim 7, wherein the anti-aliasing system is configured to adjust the alignment of the scan direction with respect to the sensor direction in response to a user input.

12. The wafer inspection system of claim 7, wherein the anti-aliasing equipment further comprises:

a controller configured to adjust the alignment of the scan direction with respect to the sensor direction.

13. The wafer inspection system of claim 7, wherein the anti-aliasing system is further configured to desynchronize a scan rate from the selected sample clock rate to blur the image data in the scan direction.

14. A method for suppressing aliasing in a wafer inspection system comprising:
    translating a wafer across a field of view of a sensor matrix at a scan rate in a scan direction to create a scanned image of the wafer;
    magnifying the scanned image;
    acquiring image data from the magnified scanned image with the sensor matrix in a sensor direction at a sample clock rate;
    generating integrated image data with the acquired image data;
    generating a pixilated image of the wafer from the integrated image data, wherein at least some pixels of the pixilated image correspond to a region of the wafer;
    desynchronizing the scan rate from the sample clock rate to blur the image data in the scan direction; and
    detecting wafer defects by analyzing the pixilated image.

15. The method of claim 14, further comprising:
    adjusting the sample clock rate of the time integration delay sensor.

16. The method of claim 14, further comprising:
    adjusting the scan rate of a wafer conveyor, the wafer conveyor configured to translate the wafer across a field of view at the scan rate along the scan direction to create the scanned image of the wafer.

17. The method of claim 14, further comprising:
    adjusting the magnification applied by the imaging optics.

18. A method for suppressing aliasing in an inspection system comprising:
    translating a sample across a field of view of a sensor matrix at a scan rate in a scan direction to create a scanned image of the sample;
    magnifying the scanned image;
    acquiring image data from the magnified scanned image with the sensor matrix in a sensor direction at a sample clock rate;
    generating integrated image data with the acquired image data;
    generating a pixilated image of the wafer from the integrated image data, wherein at least some pixels of the pixilated image correspond to a region of the wafer;
    adjusting the alignment of the scan direction with respect to the sensor direction to blur the image data in a cross-scan direction orthogonal to the scan direction; and
    detecting sample defects by analyzing the pixilated image.

19. The method of claim 18, further comprising:
    adjusting the alignment of the time integration delay sensor.

20. The method of claim 18, wherein further comprising:
    adjusting the alignment of a sample conveyor, the sample conveyor configured to translate the sample across a field of view at the scan rate along the scan direction to create the scanned image of the sample.

21. The method of claim 18, further comprising:
    optically rotating the scanned image prior to sampling.

22. The method of claim 18, further comprising:
    desynchronizing the scan rate from the sample clock rate to blur the image data in the scan direction.

* * * * *